US005470313A

United States Patent [19]
Crocker et al.

[11] Patent Number: 5,470,313
[45] Date of Patent: Nov. 28, 1995

[54] VARIABLE DIAMETER BALLOON DILATATION CATHETER

[75] Inventors: Michael Crocker, Mission Viejo, Calif.; John McB. Hodgson, Cleveland, Ohio; Girma Kebede, Lake Forest, Calif.

[73] Assignee: Cardiovascular Dynamics, Inc., Irvine, Calif.

[21] Appl. No.: 201,935

[22] Filed: Feb. 24, 1994

[51] Int. Cl.⁶ .................................................. A61M 25/00
[52] U.S. Cl. ........................................................ 604/96
[58] Field of Search .................... 604/96, 101; 606/192, 606/193, 194

[56] References Cited

U.S. PATENT DOCUMENTS

| | | | |
|---|---|---|---|
| 2,610,626 | 9/1952 | Edwards | 604/96 |
| 3,701,351 | 10/1972 | Harvey | 606/192 |
| 4,733,665 | 3/1988 | Palmaz | 606/191 |
| 4,777,951 | 10/1988 | Cribier et al. | |
| 4,896,670 | 1/1990 | Crittendon | |
| 4,906,244 | 3/1990 | Pinchuk et al. | |
| 4,921,483 | 5/1990 | Wijay et al. | |
| 4,981,478 | 1/1991 | Evard et al. | |
| 5,049,132 | 9/1991 | Schaffer et al. | |
| 5,108,369 | 4/1992 | Ganguly et al. | |
| 5,108,415 | 4/1992 | Pinchuk et al. | |
| 5,176,661 | 1/1993 | Evard et al. | |
| 5,195,969 | 3/1993 | Wang et al. | |
| 5,197,978 | 3/1993 | Hess | 606/194 |
| 5,207,700 | 5/1993 | Euteneuer | |
| 5,219,355 | 6/1993 | Parodi et al. | 604/96 |
| 5,222,966 | 6/1993 | Perkins et al. | |
| 5,246,421 | 9/1993 | Saab | |
| 5,250,069 | 10/1993 | Nobuyoshi et al. | |
| 5,250,070 | 10/1993 | Parodi | |
| 5,270,086 | 12/1993 | Hamlin | |
| 5,273,536 | 12/1993 | Savas | |
| 5,304,132 | 4/1994 | Jang | 606/192 |
| 5,320,634 | 6/1994 | Vigil et al. | 606/194 |
| 5,338,298 | 8/1994 | McIntyre | |
| 5,348,538 | 9/1994 | Wang et al. | |
| 5,352,199 | 10/1994 | Tower | |
| 5,358,486 | 10/1994 | Seab | 606/194 |

FOREIGN PATENT DOCUMENTS

| | | |
|---|---|---|
| 358117 | 3/1990 | European Pat. Off. |
| 592885 | 4/1994 | European Pat. Off. |
| 597465 | 5/1994 | European Pat. Off. |
| 9402193 | 2/1994 | WIPO |

Primary Examiner—John D. Yasko
Assistant Examiner—Manuel Mendez
Attorney, Agent, or Firm—Knobbe, Martens, Olson & Bear

[57] ABSTRACT

A dilatation catheter includes an inflation balloon having a variable diameter inflation profile. The balloon has a first inflation profile, in which it exhibits a substantially cylindrical central working profile. The first inflation profile of the balloon is achieved by inflating the balloon to a first inflation pressure. The balloon has a second inflation profile which is achieved by increasing the inflation pressure to a second, higher pressure. In the second inflation profile, a proximal segment and a distal segment of the balloon have a first inflated diameter and a central focal segment, separating the proximal and distal segments, has a second inflated diameter, such that the second inflated diameter is greater than the first inflated diameter.

13 Claims, 3 Drawing Sheets

VARIABLE DIAMETER BALLOON DILATATION CATHETER

BACKGROUND OF THE INVENTION

The present invention relates to catheters for insertion into a body lumen. More particularly, the present invention relates to a "focal" balloon dilatation catheter for use in the vascular system.

Prior art vascular dilatation balloons on typical dilatation catheters tend to fall into one of two broad classes. Most are considered noncompliant balloons, formed from a generally nondistensible material such as polyethylene. The perceived advantage of the noncompliant balloons is that they exhibit a substantially uniform exterior inflated profile which remains substantially unchanged upon incremental increases in inflation pressure. In theory, noncompliant balloons are advantageous because they allow the introduction of increased inflation pressure to break particularly calcified lesions, yet retain a predictable inflated profile so that damage to the surrounding native lumen is minimized.

Certain compliant balloons are also known in the art. A compliant balloon is one which is able to grow in diameter in response to increased inflation pressure. One difficulty with compliant balloons, however, is that inflation within a difficult lesion can cause the balloon to inflate around the plaque to produce a generally hourglass-shaped inflated profile. This can result in damage to the native vessel adjacent the obstruction, while at the same time failing to sufficiently alleviate the stenosis.

Therefore, there exists a need in the art for a vascular dilatation catheter with a balloon which is able to grow in diameter in response to increased inflation pressure, and which expands in a predictable inflation profile while minimizing any damage to the native vessel.

SUMMARY OF THE INVENTION

There is provided in accordance with one aspect of the present invention a balloon catheter, such as for performing balloon dilatation procedures in a body lumen. The catheter comprises an elongate flexible tubular body, and an inflatable balloon on the tubular body. The balloon is inflatable to a first diameter, and at least one portion of the balloon is inflatable to a second, larger diameter. In one embodiment, a proximal end and a distal end of the balloon are inflatable to a first diameter and a central segment of the balloon is inflatable to both the first diameter and also to a second greater diameter. Preferably, inflation to the first diameter is achieved by inflation to a first pressure, and inflation to the second diameter is achieved by inflation to a second, higher pressure. In one embodiment, the catheter comprises proximal and distal expansion limiting bands positioned on the proximal end and distal end of the inflation balloon to limit expansion of the proximal end and the distal end of the inflation balloon at the first diameter.

In accordance with a further aspect of the present invention, there is provided a method of treating a site in a body lumen. The method comprises the steps of providing a catheter of the type having an elongate, flexible, tubular body and a dilatation balloon on the body. Preferably, a proximal segment and a distal segment of the balloon are inflatable to a first diameter and a central segment of the balloon is inflatable to a second greater diameter. The catheter is positioned within a body lumen so that the balloon is adjacent a treatment site. The balloon is inflated to a first inflation profile, wherein the proximal segment, the distal segment and the central segment are inflated to the first inflation diameter, to treat the site. The balloon is thereafter inflated to a second inflation profile, wherein the proximal segment and the distal segment are inflated to the first inflation diameter and the central segment is inflated to the second inflation diameter, to further treat the site.

Further features and advantages of the present invention will become apparent to one of skill in the art in view of the Detailed Description of Preferred Embodiments which follows, when considered together with the attached drawings and claims.

DETAILED DESCRIPTION OF THE PREFERRED EMBODIMENTS

Figure 1:
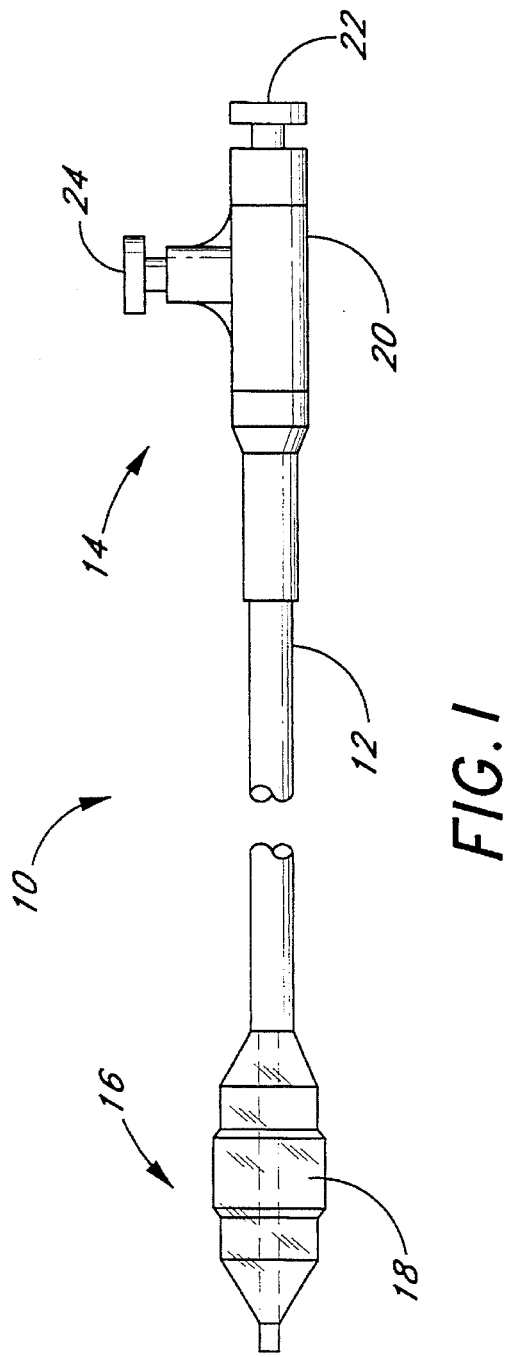
FIG. 1 is a schematic view of a preferred embodiment of a variable diameter inflation catheter of one aspect of the present invention, in the second inflation configuration.
Figure 4:
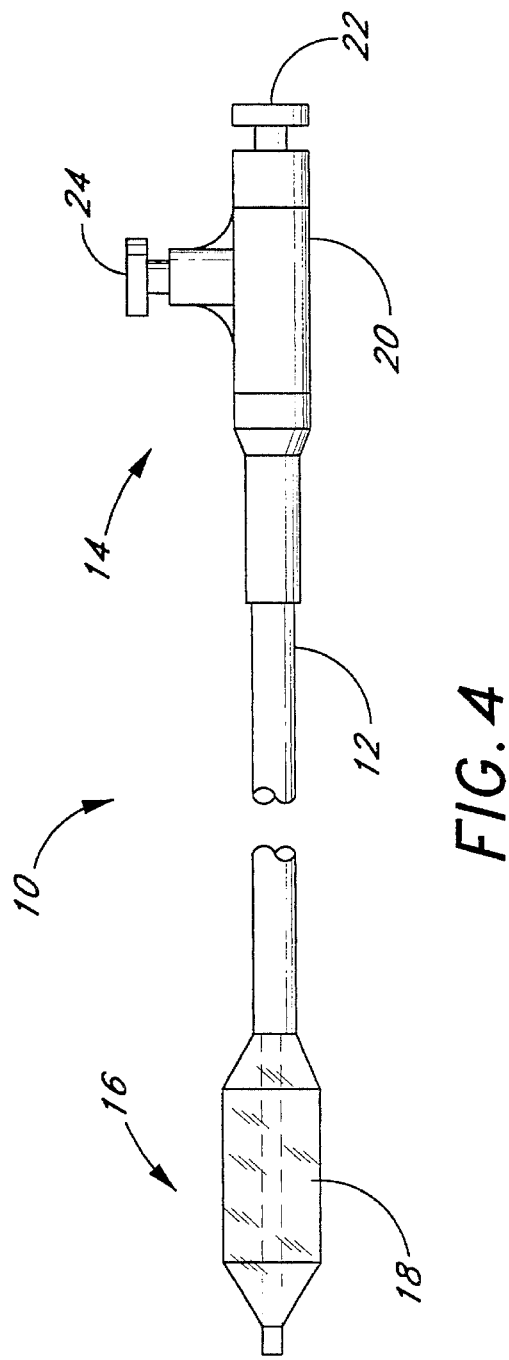
FIG. 4 is a schematic view of the embodiment of FIG. 1, shown in the first inflation configuration.

Referring to FIG. 1, there is disclosed a variable diameter inflation catheter 10 in accordance with of one aspect of the present invention. Catheters embodying additional features known in the vascular dilatation art, such as implantable stents, drug delivery, perfusion and dilatation features, or any combination of these features, can be used in combination with the focal balloon of the present invention as will be readily apparent to one of skill in the art in view of the disclosure herein.

The catheter 10 generally comprises an elongate tubular body 12 extending between a proximal control end 14 and a distal functional end 16. The length of the tubular body 12 depends upon the desired application. For example, lengths in the area of about 120 cm to about 140 cm are typical for use in percutaneous transluminal coronary angioplasty applications.

The tubular body 12 may be produced in accordance with any of a variety of known techniques for manufacturing balloon-tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall, as is understood in the catheter and guide wire arts.

In general, tubular body 12, in accordance with the present invention, is provided with a generally circular cross-sectional configuration having an external diameter within the range of from about 0.03 inches to about 0.065 inches. In accordance with one preferred embodiment of the invention, the tubular body 12 has an external diameter of about 0.042 inches (3.2 f) throughout most of its length. Alternatively, generally triangular or oval cross-sectional configurations can also be used, as well as other noncircular configurations, depending upon the number of lumen extending through the catheter, the method of manufacture and the intended use.

In a catheter intended for peripheral vascular applications, the tubular body 12 will typically have an outside diameter within the range of from about 0.039 inches to about 0.065 inches. In coronary vascular applications, the tubular body 12 will typically have an outside diameter within the range of from about 0.026 inches to about 0.045 inches. Diameters outside of the preferred ranges may also be used, provided that the functional consequences of the diameter are acceptable for the intended purpose of the catheter. For example, the lower limit of the diameter for tubular body 12 in a given application will be a function of the number of fluid or other functional lumen, support structures and the like contained in the catheter, and the desired structural integrity.

Tubular body 12 must have sufficient structural integrity (e.g., "pushability") to permit the catheter to be advanced to distal arterial locations without buckling or undesirable bending of the tubular body 12. The ability of the body 12 to transmit torque may also be desirable, such as in embodiments having a drug delivery capability on less than the entire circumference of the delivery balloon. Larger diameters generally have sufficient internal flow properties and structural integrity, but reduce perfusion in the artery in which the catheter is placed. Increased diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 1, the distal end 16 of catheter 10 is provided with at least one inflation balloon 18 having a variable diameter. The proximal end 14 of catheter 10 is provided with a manifold 20 having a plurality of access ports, as is known in the art. Generally, manifold 20 is provided with a guide wire port 22 in an over the wire embodiment and a balloon inflation port 24. Additional access ports are provided as needed, depending upon the functional capabilities of the catheter 10. The balloon 18 can also be mounted on a rapid exchange type catheter, in which the proximal guidewire port 22 would be unnecessary as is understood in the art. In a rapid exchange embodiment, the proximal guidewire access port is positioned along the length of the tubular body 12, such as between about 4 and about 20 cm from the distal end of the catheter.

Figure 2:
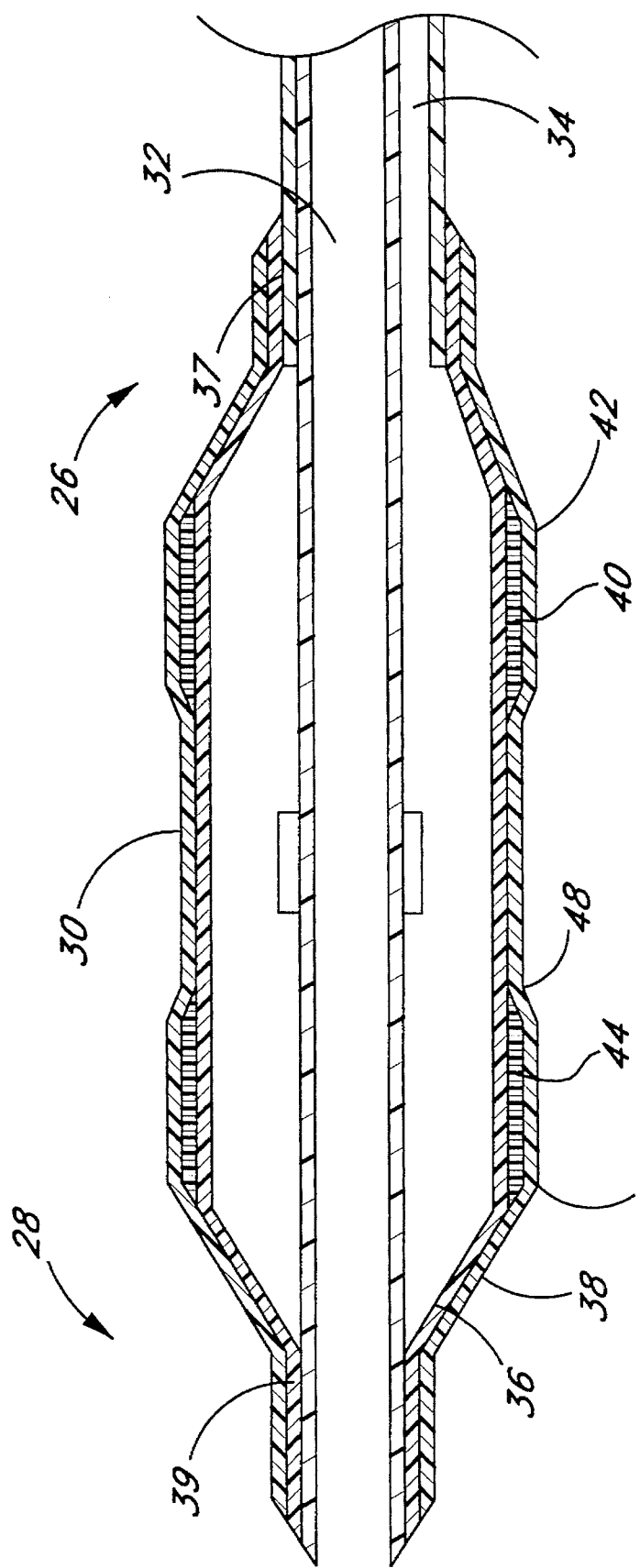
FIG. 2 is a partial cross-sectional view of a preferred embodiment of the variable diameter inflation catheter at a first inflation profile.
Figure 3:
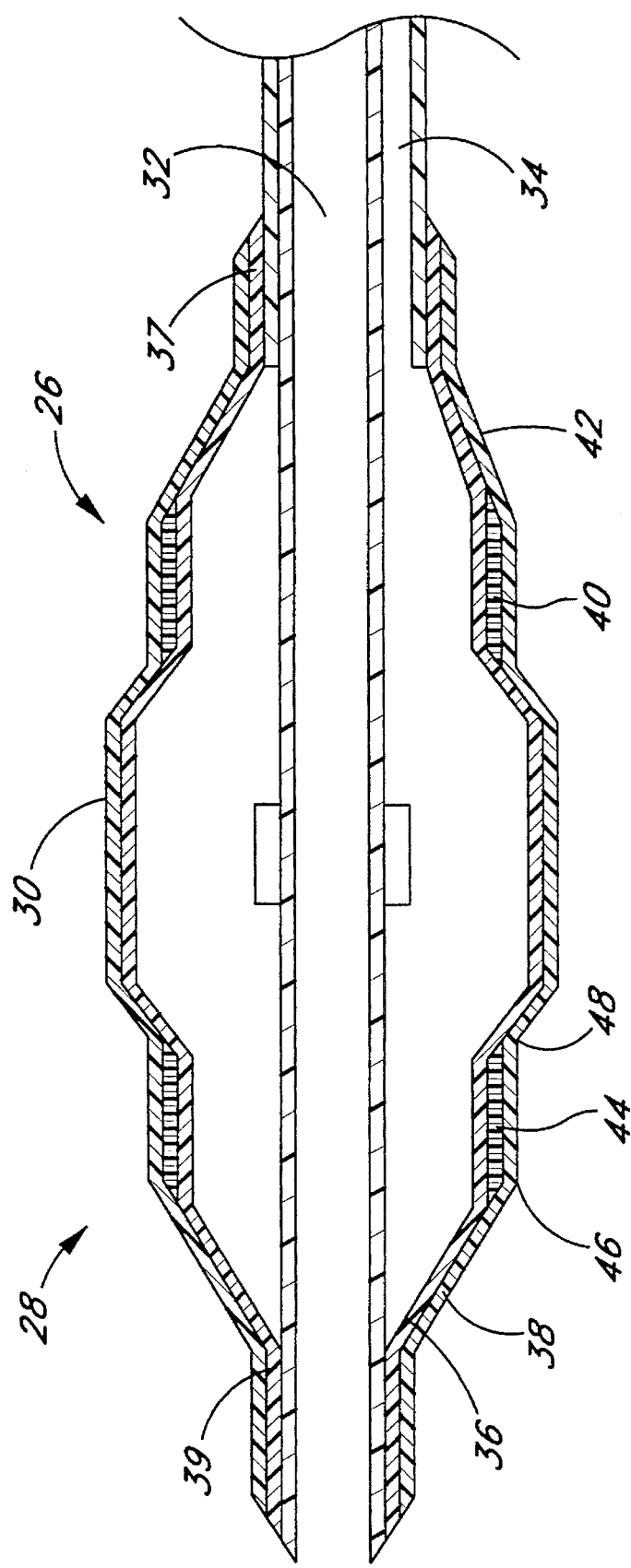
FIG. 3 is a partial cross-sectional view of a preferred embodiment of the variable diameter inflation catheter at a second inflation profile.

Referring to FIGS. 2 and 3, the two-step inflation profile of the inflation balloon 18 is illustrated. In FIG. 2, the balloon 18 is illustrated at a first inflation profile, in which it exhibits a substantially cylindrical central working profile. The dimensions in FIG. 2 are exaggerated to illustrate a proximal segment 26 and a distal segment 28 which are axially separated by a central focal segment 30. However, as will be understood by one of ordinary skill in the art, when the balloon 18 is inflated to the first inflation profile, the exterior of the balloon 18 preferably exhibits a substantially smooth cylindrical working profile.

In FIG. 3, the inflation balloon 18 is illustrated at a second inflation profile. The proximal segment 26 and the distal segment 28 of the balloon are separated by the central focal segment 30 having a greater diameter. The configuration of FIG. 2 is achieved by inflating the balloon 18 to a first inflation pressure, while the configuration of FIG. 3 is achieved by increasing the inflation pressure to a second, higher pressure as will be discussed below.

The details of one preferred embodiment of the variable diameter inflation catheter 10 are discussed with reference to FIGS. 2 and 3. Preferably, the tubular body 12 is provided with at least a guidewire lumen 32 extending all the way through the balloon 18, and an inflation lumen 34 extending into the proximal end of the balloon 18.

In the illustrated embodiment, an inner balloon 36 is disposed coaxially within an outer balloon 38. A substantially nondistensible expansion limiting band 40 is disposed in between the balloons 36 and 38 adjacent a proximal annular shoulder 42, to limit the radial expansion of the balloon 18. Similarly, a distal expansion limiting band 44 is disposed between the inner balloon 36 and outer balloon 38 adjacent a distal annular shoulder 46.

Expansion limiting bands 40 and 44 or other inflation limiting structures can be provided in any of a variety of ways which will be well-understood by one of skill in the art in view of the disclosure herein. For example, in one embodiment, the bands 40 and 44 each comprise a tubular section of polyester, each having an axial length of about 5 mm, a diameter of about 2.5 mm and a wall thickness of about 0.0003 inches. Other generally nondistensible materials such as nylon, polyimide, Kevlar fiber, cross-linked polyethylene, polyethylene terephthalate and others, may be utilized to accomplish the expansion-limiting effect.

The expansion limiting characteristics can be achieved by the addition of a structure that is discrete from the balloon, or by modifying the expansion properties of the balloon material itself. For example, the balloon can be provided with zones of differing wall thickness, or zones having different levels of cross linking as will be discussed.

In general, the bands 40 and 44 must be of a sufficient thickness or structural integrity for the particular material used to substantially withstand inflation under the pressures normally utilized in the context of dilatation catheters. However, the bands 40 and 44 are preferably thin enough to provide a substantially smooth exterior surface of the balloon 18.

Preferably, as illustrated in FIGS. 2 and 3, the expansion-limiting bands 40 and 44 are sandwiched between the inner balloon 36 and the outer balloon 38. In alternative embodiments, the expansion-limiting bands 40 and 44 or other inflation limiting structures may be coated or mounted on the exterior surface of the balloon 18, the interior surface of the balloon 18 or within the wall of the balloon 18. Balloon 18 can be provided with two or more layers as illustrated, or with only a single layer as will be discussed.

The axial length of the bands 40 and 44 can be varied widely depending upon the dimensions and the objectives of the catheter 10 as will be apparent to one of ordinary skill in the art. Further, the proximal band 40 and distal band 44 need not be of similar lengths. In general, however, some examples of dimensions which are useful in the coronary angioplasty dilatation environment are reproduced in Table 1 below, in which A represents the axial length of the balloon 18 between proximal shoulder 42 and distal shoulder 46, B represents the axial distance between distal shoulder 46 and transition point 48, and C represents the axial length of the central focal segment 30. The dimensions of Table 1 are exemplary only, and the present invention can be accomplished using a wide variety of other dimensions as will be apparent to one of skill in the art.

TABLE 1

| A | B | C |
| --- | --- | --- |
| 20 mm | 5 mm | 10 mm |
| 30 mm | 5 mm | 20 mm |

TABLE 1-continued

| A | B | C |
| --- | --- | --- |
| 40 mm | 5–10 mm | 20–30 mm |

The catheter 10 illustrated in FIGS. 2 and 3 can be manufactured in accordance with any of a variety of techniques which will be appreciated by one of ordinary skill in the art in view of the disclosure herein. In the following disclosure, particular materials and dimensions will be used as an example only, and other dimensions and materials can be selected depending upon the desired characteristics of the finished product.

In one particular method of manufacturing, a low density polyethylene extrusion stock tube having an inside diameter of about 0.018 inches and an outside diameter of about 0.043 inches is used for the inner and outer balloons 36, 38.

The polyethylene stock tubing is cross-linked by exposure to an electron beam in accordance with techniques well known in the art. A test segment of the cross-linked stock tubing is free blown up to 3.0 mm in diameter. If the cross-linked stock tubing can be free blown to a diameter greater then 3.0 mm, the stock tubing is cross-linked again and retested until the desired free blow diameter is achieved.

The appropriately cross-linked stock tubing is then blown to a diameter of 2.5 mm within a teflon capture tube (not shown) which acts to mold the balloon to its desired first inflation diameter. The teflon capture tube is a generally tubular body which has approximately the same inside diameter as the desired inflation diameter of the balloon. The teflon capture tube is heated by any of a number of heating means such as electric coils or a furnace to a temperature which is sufficient to mold the balloon to the desired inflation diameter. In this case, the cross-linked polyethylene balloon is preferably heated to a temperature of about 300° F. The teflon chamber is then cooled to a temperature below the softening temperature of the balloon. Once cooled, the balloon is deflated and removed from the capture tube.

A section of inflation balloon material is thereafter stretched with application of heat to neck down the proximal and distal ends 37, 39 to a thickness of about 0.001 inches and a diameter which relatively closely fits the portion of the tubular catheter body 12 to which it is to be sealed.

The balloon is then attached to the tubular body 12 by any of a variety of bonding techniques known to one of skill in the art such as solvent bonding, thermal adhesive bonding or by heat shrinking/sealing. The choice of bonding techniques is dependent on the type of balloon material and tubular body material used to form the catheter 10.

In one particular method of manufacture, inner balloon 36 and outer balloon 38 are attached to the catheter body 10. The proximal necked end 37 of the inner balloon 36 is heat sealed around the catheter body 12. The distal necked end 39 of the inner balloon 36 is thereafter heat sealed around the distal end 16 of the catheter body 12. In general, the length of the proximal end 37 and the distal end 39 of the inner balloon 36 which is secured to the catheter body 12 is within the range of from about 3 mm to about 10 mm, however the proximal and distal balloon necked ends 37, 39 are as long as necessary to accomplish their functions as a proximal and distal seal.

Expansion limiting bands 40 and 44 are respectively positioned at the proximal segment 26 and the distal segment 28 of the inner balloon 236 and may be bonded or otherwise secured to the inner balloon 36. The outer balloon 38 is thereafter be mounted to the catheter body 12 in a similar manner as the inner balloon 36, following "necking down" of the proximal and distal axial ends of the outer balloon 38 by axial stretching under the application of heat. The outer balloon 38 is advanced axially over the inner balloon 36 and the expansion limiting bands 40 and 44. The outer balloon 38 may thereafter be bonded to the inner balloon 36, and to the expansion limiting bands 40 and 44 by any of a variety of bonding techniques such as solvent bonding, thermal adhesive bonding or by heat sealing also depending on the type of balloon material used. Alternatively, the expansion limiting bands are simply entrapped between the balloons without any bonding or adhesion.

In a preferred embodiment, the inner balloon and the outer balloon 36, 38 are both cross-linked polyethylene balloons which are difficult to bond together using conventional solvents. If sealing is desired, the inner balloon 38 and the outer balloon 38 are heat sealed together as described below. In another embodiment, the inner balloon 36 and outer balloon 38 are secured together through the use of a UV-curable adhesive.

The inner balloon 36 and the outer balloon 38, once mounted to the catheter body 12, can be heat sealed together in a heating chamber (not shown) such as a Teflon capture tube. Inner balloon 36 and outer balloon 38 are inflated in the chamber until the inner balloon and the outer balloon inflate to the first inflation diameter. The heating chamber is heated by any of a number of heating means such as electric coils or a furnace to heat air to a temperature which is sufficient to bond the two balloons 36, 38 together. In this case, the cross-linked polyethylene balloons are preferably heated to a temperature of about 300° F. within the chamber which causes both balloons 36, 38 to seal together to form a double walled variable diameter inflation balloon 18. The chamber is then cooled to a temperature below the softening temperature of the inner and outer balloons 36 and 38. Once cooled, the variable diameter balloon 18 is deflated and the catheter 10 is removed from the chamber.

It will be apparent to one of skill in the art, that it is possible to attach the inner balloon 36 and the outer balloon 38 to the catheter body 12 without adhesively bonding or otherwise securing the two balloons together. In this case, the two balloons will respond to the applied inflation pressure with the inner balloon 36 forcing the outer balloon 38 to simultaneously inflate both balloons 36, 38. The expansion limiting bands 40 and 44 can be merely sandwiched between the inner balloon 36 and the outer balloon 38 and do not in this embodiment need to be bonded to either balloon.

The variable diameter balloon design of the present invention can also be accomplished with a single layer balloon or a double layer balloon without the inclusion of additional expansion limiting bands. This is accomplished by decreasing the relative compliance of the zones of the balloon that are intended to remain at the first inflated diameter. For example, polyethylene extrusion stock is cross-linked to 3.0 mm and blown into a mold of a diameter of about 2.5 mm as described above to form a balloon. The balloon is attached to the catheter as described above. The balloon is inflated and the central focal segment 30 of the balloon on the catheter 10 is masked such as with a steel clamp or other mask known in the art to block electron beam penetration, leaving the proximal segment 26 and the distal segment 28 of the balloon exposed. The inflated proximal segment 26 and distal segment 28 of the balloon 18 are exposed again to an electron beam source to further cross-link the segments 26, 28 at the 2.5 mm diameter. Balloons manufactured in this manner have been found to exhibit a relatively highly compliant central zone and relatively less complaint axial end zones in a manner that achieves the two-step dilatation as illustrated in FIGS. 2 and 3.

Preferably, however, a dual balloon structure is used, which incorporates the expansion limiting bands as illustrated in FIGS. 2 and 3. Balloons 18 made in accordance with the design illustrated in FIGS. 2 and 3 have been found to exhibit the inflation pressure profile illustrated in Table 2.

TABLE 2

| PRESSURE | CENTRAL SEGMENT DIAMETER | PROXIMAL AND DISTAL SEGMENT DIAMETER |
|---|---|---|
| 6 atm | 2.5 mm | 2.5 mm |
| 7 atm | 2.6 mm | 2.5 mm |
| 8 atm | 2.7 mm | 2.5 mm |
| 9 atm | 2.8 mm | 2.5 mm |
| 10 atm | 2.9 mm | 2.5 mm |
| 11 atm | 3.0 mm | 2.5 mm |
| 12 atm | 3.1 mm | 2.5 mm |
| 13 atm | 3.2 mm | 2.5 mm |
| 14 atm | 3.3 mm | 2.6 mm |

The inflation pressure profile of the variable diameter inflation balloon 18 illustrated in Table 2 provides an example of the manner in which a balloon 18 made in accordance with the foregoing method is inflated with the application of increased pressure. Initially, the central segment 30 and the proximal and distal segments 26, 28 of the balloon 18 inflate together as the pressure increases. When the pressure reaches 6 atm, for example, the diameter of the proximal and distal segments 26, 28 and the central segment 30 of the balloon all remain at about 2.5 mm. At 11 atm, the diameter of the central segment 30 of the balloon 18 has grown to about 3 mm while the proximal and distal segments 26, 28 remained inflated to the first diameter of 2.5 mm. The diameter of the central section 30 of the balloon 18 will continue to increase until the burst pressure of the balloon 18 is reached. In one prototype, the burst pressure was approximately 16 atm at normal body temperature.

Both the first inflation diameter and the second inflation diameter can also be varied depending upon the desired catheter characteristics as will be understood by one of ordinary skill in the art. In a preferred embodiment, a first inflated diameter of the catheter for coronary angioplasty applications is approximately 2.5 mm. Upon an increase of pressure, this diameter grows to a second inflated diameter of approximately 3 mm in the central focal segment 30. In general, balloons can be readily constructed having a difference between the first inflation diameter and second inflation diameter anywhere within the range of from about 0.1 mm up to 1.0 mm or more, depending upon the elastic limits of the material from which the balloon was constructed. Typically, coronary angioplasty dilatation balloons will have a first diameter within the range of from about 1.5 mm to about 4.0 mm. Typical balloons for use in peripheral vascular applications will have a first inflation diameter within the range of from about 2 mm to about 10 mm.

Dilatation balloons can readily be constructed in accordance with the present invention in which entire length of the balloon from, for example, proximal shoulder 42 to distal shoulder 46 (FIG. 2) is variable from a first inflated diameter to a second larger inflated diameter in response to increasing pressure. Alternatively, balloons in accordance with the present invention can readily be constructed in which a proximal portion of the balloon is compliant so that it can grow in response to increased pressure, while a distal portion of the balloon has a fixed inflated diameter. This configuration may be desirable, for example, when the native vessel diameter is decreasing in the distal catheter direction. Positioning the catheter so that the compliant portion is on the proximal (larger diameter) portion of the vessel may minimize damage to the vessel wall in certain applications. Alternatively, the compliant segment can readily be positioned on the distal end of the balloon with a substantially fixed inflated diameter segment on the proximal end of the balloon.

A variable diameter balloon 18 made in accordance with the foregoing designs has been found to benefit certain conventional percutaneous transluminal coronary angioplasty (PTCA) procedures. In accordance with the method of the present invention, the variable diameter balloon 18 is percutaneously advanced and positioned such that the central segment 30 of the balloon 18 is adjacent a vascular treatment site. Generally, the treatment site is a stenosis such as due to a plaque or thrombus. The variable diameter balloon 18 is inflated to a first inflation profile to begin dilation of the stenosis. Preferably, the first inflation profile is achieved by applying up to about 6 atm of pressure to the balloon 18. At the first inflation profile, the entire balloon is inflated to the inner diameter of the vessel, thus restoring patency to the vascular lumen. In one embodiment, the variable diameter balloon 18 is inflated to a first inflation diameter, of about 2.5 mm, at an inflation pressure of 6 atm. The first inflation diameter is preferably about the native diameter of the vessel.

As additional pressure is applied to the variable diameter balloon 18, a second inflation profile is achieved wherein the central segment 30 of the balloon 18 expands beyond the diameter of the first inflation profile to a second inflation diameter, while the proximal segment 26 and the distal segment 28 remain at the first inflation diameter. As the pressure applied to the variable diameter balloon 18 increases, the diameter of the central segment 30 of the balloon 18 extends past the native diameter of the vessel to the second inflation diameter. Utilizing this method, and depending upon the balloon size selected, the stenosis is compressed to a point which is beyond the native diameter of the vessel. In a preferred embodiment, at an applied pressure of 11 atm the diameter of the central segment 30 of the balloon 18 at the second inflation diameter is 3 mm and the diameter of the proximal end 26 and the distal end 28 at the first inflation diameter is 2.5 mm. Second inflation diameters in between the first inflation diameter and the maximum inflation diameter can be readily achieved by controlling inflation pressure, as illustrated for one embodiment in Table 2, above.

After the stenosis is compressed to or beyond the native diameter of the vessel, the balloon is evacuated and the catheter withdrawn. Alternatively, if desired, the pressure is reduced until the balloon 18 resumes the first inflation profile. At this point, the balloon 18 may be held at the first inflation diameter for short periods to continue to maintain patency of the lumen if short term rebound is a concern. This post dilatation step is preferably accomplished using a catheter having perfusion capabilities. Finally, the remaining pressure applied to the balloon 18 is reduced causing the variable diameter balloon 18 to deflate. The catheter is then extracted from the vessel utilizing conventional PTCA procedures.

In accordance with a further aspect of the present invention, there is provided a method of implanting a tubular stent within a body lumen. Tubular stents of the type adapted to be carried to a vascular site on a balloon catheter, and for expansion from a first insertion diameter to a second implanted diameter are well-known in the art.

In accordance with the method of implanting a tubular stent, an expandable stent is positioned about the deflated balloon of a variable diameter balloon catheter in accordance with the present invention. The balloon is thereafter percutaneously inserted into the vascular system and transluminally advanced to position the stent at the treatment site. The balloon is thereafter inflated to at least a first inflation configuration, wherein the balloon exhibits a substantially cylindrical profile throughout its axial length. Thereafter, the balloon is optionally inflated to a second inflation profile, thereby inflating at least a portion of the stent to a second, greater diameter. Depending upon the etiology of the underlying condition, the central region of the stent may preferably be inflated to a larger diameter than either of the axial ends of the stent.

Alternatively, the axial length of the stent is selected to approximately equal the axial length of the focal zone on the inflation balloon. In this manner, the inflation balloon within the stent is expandable to a diameter slightly larger than the native diameter of the adjacent vessel. This permits subsequent overgrowth of endothelium along the interior wall of the stent while still leaving a lumen having an interior diameter within the stent approximately equal to the native diameter of the lumen adjacent the stent.

In accordance with a further aspect of the present invention, the variable diameter balloon is utilized to "tack down" a previously positioned tubular stent. In accordance with this aspect of the present invention, a tubular stent is identified within a body lumen. The focal balloon is positioned within the stent in accordance with conventional PTCA procedures, and the balloon is inflated so that the central, focal section enlarges the diameter of at least a first portion of the stent. The balloon is thereafter reduced in diameter, and, preferably, repositioned within a second region within the stent and then reinflated to expand at least the second region of the stent. Expansions of this type can be repeated until the stent has been expanded as desired. The balloon is thereafter evacuated and removed from the patient.

In accordance with a further aspect of the present invention, there is provided a method of percutaneous transluminal angioplasty in which multiple lesions of differing sizes are dilated without removing the catheter from the body. In accordance with this aspect of the present invention, the variable diameter balloon is positioned within a first stenosis in accordance with conventional PTCA techniques. The balloon is dilated to a sufficient diameter to restore patency to the vascular lumen. The balloon is thereafter deflated, and repositioned within a second stenosis in the vascular system. The balloon is inflated to restore patency of the vessel in the region of the second stenosis. Optionally, the balloon may be deflated, and repositioned within a third stenosis in the body lumen. The balloon is then inflated to a sufficient diameter to restore patency in the body lumen in the region of the third stenosis. Four or more lesions can be treated seriatim in this manner.

Preferably, the balloon is inflated to a first diameter in the first stenosis, and to a second, different diameter, in the second stenosis. In this manner, multiple dilatations at different diameters can be accomplished utilizing the balloon of the present invention. This method is accomplished by supplying a first inflation pressure to the balloon while the balloon is positioned in a first position in the vascular system, and thereafter supplying a second pressure to the balloon when the balloon is in a second position in the vascular system. In accordance with the previous disclosure herein, each of the first and second inflation pressures is selected to achieve a preselected inflation diameter of the balloon.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A balloon catheter, comprising:

an elongate, flexible, tubular body; and an inflatable balloon on the tubular body, wherein a proximal segment, a central segment, and a distal segment of said balloon are inflatable to a first inflated diameter at a first inflation pressure, and where the material of said central segment expands to a second, greater inflated diameter at a second, greater inflation pressure, and said proximal and distal segments remain substantially at the first diameter at said second inflation pressure.

2. A balloon catheter as in claim 1, additionally comprising proximal and distal expansion limiting bands positioned on said proximal and distal segments of said inflation balloon to limit inflation of said proximal and said distal segments of the inflation balloon at said first diameter.

3. A method of treating a site in a body lumen, comprising the steps of:

providing a catheter of the type having an elongate, flexible, tubular body and a dilatation balloon on the body, wherein a proximal segment, a central segment, and a distal segment of said balloon are inflatable to a first diameter at a first inflation pressure, and where said central segment of said balloon is inflatable to a second greater diameter at a second, greater inflation pressure, and the proximal and distal segments remain substantially at the first diameter at said second inflation pressure;

positioning the catheter within a body lumen so that the balloon is adjacent to a treatment site;

inflating the balloon to said first inflation pressure, wherein said proximal segment, said distal segment, and said central segment are inflated to said first inflation diameter, to treat the site; and inflating the balloon to a second inflation pressure while simultaneously restraining the proximal and distal segments against further radial expansion, thereby substantially preventing said proximal segment and said distal segment from expanding beyond said first inflation diameter and expanding said central segment to said second inflation diameter, to further treat the site.

4. A multiple zone balloon catheter, comprising:

an elongate flexible tubular body;

an inflatable balloon mounted on the tubular body;

a first zone on the balloon, inflatable to a first inflated diameter at a first inflation pressure;

a second zone on the balloon, inflatable to said first inflation diameter at said first inflation pressure, and to at least one second inflation diameter at a second greater inflation pressure; and an inflation limiting structure on said first zone;

wherein said second inflation diameter is larger than said first inflation diameter, and where said first zone is prevented from radially expanding to said second inflation diameter at said second inflation pressure by the inflation limiting structure on said first zone.

5. A multiple zone balloon catheter as in claim 4, wherein said first inflated diameter is within the range of from about 1.5 mm to about 10 mm.

6. A multiple zone balloon catheter as in claim 4, wherein said inflation limiting structure comprises at least one expansion limiting band on the first zone of the balloon to restrain expansion of the first zone.

7. A multiple zone balloon catheter as in claim 4, further comprising a third zone on the balloon, adjacent to the second zone, and inflatable to said first inflated diameter.

8. A multiple zone balloon catheter as in claim 4, wherein said first zone is positioned adjacent to and distally of said second zone.

9. A method of expanding multiple treatment sites to varying diameters within a body lumen, comprising the steps of:

providing an elongate flexible catheter having a variable diameter balloon thereon, said balloon having a first inflation profile at a first inflation pressure resulting in a substantially cylindrical balloon structure having a first inflated diameter, and at least a second inflation profile at a second greater inflation pressure wherein a portion of the balloon expands to a second, greater inflated diameter and a separate portion of the balloon does not expand to said second inflated diameter;

positioning the catheter so that the balloon is within a first treatment site;

inflating the balloon to said first diameter at said first inflation pressure to treat the site;

deflating the balloon and repositioning the balloon within a second treatment site; and inflating the balloon with a second, greater inflation pressure so that said portion inflates to a second greater diameter to treat the second treatment site.

10. A method as in claim 9, wherein said inflating the balloon to a second diameter is accomplished by introducing a different pressure into said balloon than the pressure utilized to inflate the balloon to the first diameter.

11. A method of implanting a tubular stent within a body lumen using a variable diameter balloon, comprising the steps of:

providing an elongate flexible tubular body having an inflatable balloon thereon, said balloon inflatable to a first diameter at a first inflation pressure to produce a substantially cylindrical balloon structure, and a focal portion of said balloon additionally inflatable to a second, larger diameter at a second, greater inflation pressure;

positioning an expandable tubular stent on the balloon;

positioning the balloon within a body lumen adjacent a treatment site;

inflating the balloon to the first inflation diameter to expand the tubular stent; and thereafter increasing the inflation pressure to said second inflation pressure such that said focal portion of the balloon inflates to the second larger diameter to further expand the tubular stent.

12. A method as in claim 11, further comprising the step of repositioning the balloon within the tubular stent and inflating the balloon to the second diameter for at least a second time.

13. A method of enlarging the diameter of an expandable tubular stent within a body lumen, comprising the steps of:

locating an expandable tubular stent in a position within a body lumen;

positioning an inflatable balloon within the stent, said balloon inflatable to a first inflation diameter at a first inflation pressure to produce a substantially cylindrical balloon structure, and a portion of said balloon additionally inflatable to a second, larger diameter at a second, greater inflation pressure;

inflating the balloon with said first inflation pressure to said first diameter within the stent; and increasing the inflation pressure to said second inflation pressure such that said portion of the balloon is inflated to the second, larger diameter within the stent.

* * * * *